United States Patent [19]

Nasuno et al.

[11] 4,390,524
[45] Jun. 28, 1983

[54] MAKEUP COMPOSITIONS IN CAKE FORM INCLUDING FIBROIN-COATED AND OILY MATERIAL-COATED PIGMENTS

[75] Inventors: Toshihiro Nasuno, Odawara; Kiyoshi Otoi, Nagano, both of Japan

[73] Assignee: Kanebo, Ltd., Tokyo, Japan

[21] Appl. No.: 242,803

[22] Filed: Mar. 11, 1981

[30] Foreign Application Priority Data

Mar. 15, 1980 [JP] Japan ................................ 55-33302

[51] Int. Cl.³ .................. A61K 7/02; A61K 7/021; A61K 7/025; A61K 7/035
[52] U.S. Cl. ................................ 424/63; 106/308 F; 106/308 P; 106/309; 424/64; 424/69; 424/359; 424/365; 424/DIG. 5
[58] Field of Search .................. 424/63, 64, 69, 359, 424/365, DIG. 5; 106/308 N, 308 P, 308 F, 309

[56] References Cited
FOREIGN PATENT DOCUMENTS 514070 10/1939 United Kingdom ................ 424/69

OTHER PUBLICATIONS

Nasuno et al., Chem. Abs., vol. 90, 1979, Ab. No. 90:76421s.
Nishi et al., Chem. Abs., vol. 77, 1972, Ab. No. 103121j.
Nasuno, Chem. Abs., vol. 93, 1980, Ab. No. 53795q.

Primary Examiner—Anna P. Fagelson
Attorney, Agent, or Firm—Flynn, Thiel, Boutell & Tanis

[57] ABSTRACT

A makeup composition is disclosed which consists essentially of a homogeneous mixture of a fibroin-coated pigment comprising a carrier pigment in the form of finely divided particles whose surfaces are substantially coated with a film of regenerated fibroin and an oily material-coated pigment comprising a carrier pigment in the form of finely divided particles whose surfaces are substantially coated with an oily material and which is in the form of powder (i.e., loose powder) or a cake (i.e., pressed powder). This makeup composition in powder or cake form has excellent properties such as adhesion to the skin, moisture retention, durability of the makeup, fragrance retention, stability and the like, causes no irritation to the skin, and can give an agreeable feeling (i.e., a moist and silkily smooth feeling) and a natural silk-like gloss to the skin. In particular, the makeup composition in cake form can be smoothly applied to the skin during all seasons by using a wet applicator (e.g., a wet puff) and/or a dry applicator (e.g., a dry puff). It is so stable that no agglomeration or caking of its particles results.

19 Claims, No Drawings

MAKEUP COMPOSITIONS IN CAKE FORM INCLUDING FIBROIN-COATED AND OILY MATERIAL-COATED PIGMENTS

BACKGROUND OF THE INVENTION (1) Field of the Invention

This invention relates to makeup compositions which consist essentially of homogeneous mixtures of a fibroin-coated pigment comprising a carrier pigment substantially coated with a film of regenerated fibroin formed by coagulating a solution of silk fibroin (hereinafter referred to simply as fibroin) and an oily material-coated pigment comprising a carrier pigment substantially coated with an oily material, which are in the form of powder (i.e., loose powder) or cakes (i.e., pressed powder). More particularly, the invention relates to makeup compositions in powder or cake form which cause no irritation to the skin, have excellent properties such as spreadability on the skin, adhesion to the skin, feeling, moisture retention and fragrance retention, and can give a silk-like gloss and a silky feeling to the skin. Still more particularly, it relates to makeup compositions in cake form which permit the user to use a wet applicator (e.g., a wet puff) or a dry applicator (e.g., a dry puff) according to preference and can be smoothly applied to the skin during all seasons without undergoing agglomeration or caking of its particles.

(2) Description of the Prior Art

Conventional makeup compositions in powder form (e.g., face powder and the like) consist mainly of titanium dioxide, zinc white, talc, metallic soaps and precipitated calcium carbonate. However, such compositions cannot be formulated easily because slight variations in composition may cause changes in covering power, lubricity, absorbing power, water resistance and the like. It is well known that some properties (such as adhesion to the skin, spreadability on the skin, feeling, finish of the makeup, and the like) of such makeup compositions in powder form can be improved by addition of a nonionic surface-active agent having low HLB, such as polyoxyethylene glycol diesters, esters and ethers of polyhydric alcohols, and the like, to the aforesaid base materials. However, the addition of such a surface-active agent is disadvantageous in that it causes irritation to the skin. Moreover, the effect produced thereby is not always satisfactory.

In order to make a makeup composition in powder form (e.g., face powder or the like) handy to carry, the powder may be compressed into a cake and then enclosed in a case (i.e., a so-called compact). Such a makeup composition in cake form is generally known as pancake makeup or the like. In this case, however, the oily materials are applied to the skin after they have been emulsified with the aid of the water contained in the applicator (e.g., a wet puff or the like) and the surface-active agent included in the makeup composition. Thus, this makeup composition has the disadvantage that skin disorders may result from the irritant action of the surface-active agent. Moreover, when this makeup composition is handled repeatedly with a wet applicator, some components (e.g., binders and the like) may combine firmly with the pigments to result in caking of the surface layer. Then, the makeup composition fails to transfer to even a wet applicator. Furthermore, such a makeup composition in cake form must be applied to the skin exclusively by using a wet applicator (e.g., a wet puff) because it does not transfer to a dry applicator (e.g., a dry puff).

In an attempt to overcome the above-described disadvantages, U.S. Pat. No. 3,296,078 discloses a compressed face powder cake composition containing an anionic surface-active agent (e.g., sodium lauryl sulfate or the like) or a cationic surface-active agent (e.g., alkyl dimethyl benzyl ammonium chloride or the like). However, this cosmetic composition also has the disadvantage of causing irritation to the skin owing to the use of a synthetic surface-active agent. Moreover, its particles may undergo agglomeration during long-term use, so that they can hardly be handled with a dry puff.

Additional attempts to solve the problem of skin irritation by surface-active agents are found in Japanese Patent Publication No. 7066/'77 and Japanese Patent Laid-Open No. 14528/'79. The makeup compositions disclosed therein have succeeded in solving the problem, but involve other difficulties. Specifically, these makeup compositions cause no irritation to the skin because surface-active agents are absent. However, the former makeup composition cannot be used in seasons other than summer. Moreover, this makeup composition is subject to caking of its surface layer owing to the water-soluble materials coexisting with the oily materials and the pigments as well as the water contained in the applicator, and it does not permit the use of a dry applicator. In the latter makeup composition, the water-repellent silicone oils and oily binders coexisting with the pigments have no affinity for water, so that these oily materials cannot be homogeneously mixed with the water contained in the wet applicator. Accordingly, this makeup composition can neither be evenly applied to the skin nor be smoothly spread on the skin. Moreover, this makeup composition is poor in durability of the makeup because the oily materials rise to the surface under the influence of sweat or water. Even if it is applied to the skin by using a dry applicator, this strongly water-repellent makeup composition gives an oily feeling. Therefore, especially in winter when the skin has a low water content, this makeup composition can hardly be used from the viewpoint of physiology of the skin.

Thus, prior art makeup compositions in cake form are substantially unusable in seasons other than summer and scarcely have the two-way function, i.e., the function of being applicable to the skin by using both a wet applicator (e.g., a wet puff) and a dry applicator (e.g., a dry puff). Accordingly, there is a continuing demand for satisfactory makeup compositions in cake form which can exhibit the two-way function during all seasons and have excellent properties such as moisture retention, fragrance retention, affinity for the skin, spreadability on the skin, feeling, silk-like gloss and the like.

BRIEF SUMMARY OF THE INVENTION

In order to overcome the above-described disadvantages of the prior art, the present inventors have made intensive and extensive studies and have discovered that all of these disadvantages can be overcome by makeup compositions consisting essentially of a fibroin-coated pigment and an oily material-coated pigment.

Accordingly, it is one object of the present invention to provide a makeup composition in cake form which can remove the restriction on the type of applicator used thereby exhibiting the above-defined two-way function, can be smoothly applied to the skin during all seasons, causes no irritation to the skin, has excellent properties such as moisture retention, adhesion to the skin, durability of the makeup, fragrance retention, stability and the like, has an agreeable feeling (i.e., a moist, silky smooth feeling) and imparts a natural silk-like gloss to the skin.

It is another object of the present invention to provide a makeup composition in powder form which causes no irritation to the skin, has excellent properties such as moisture retention, adhesion to the skin, durability of the makeup, fragrance retention and the like, and can give an agreeable feeling and a natural silk-like gloss to the skin.

The above and other objects of the present invention are accomplished by a makeup composition consisting essentially of a homogeneous mixture of a fibroin-coated pigment and an oily material-coated pigment;

(1) the fibroin-coated pigment comprising a carrier pigment in the form of finely divided particles the surfaces of which are substantially coated with a film of regenerated fibroin;

(2) the oily material-coated pigment comprising a carrier pigment in the form of finely divided particles the surfaces of which are substantially coated with a substantially water-insoluble oily material; and (3) the composition being in the form of powder or a cake.

DETAILED DESCRIPTION OF THE PREFERRED EMBODIMENTS

The fibroin-coated pigment used in the practice of the present invention is a pigment the surfaces of which are coated with a film of regenerated fibroin formed by coagulation of a fibroin solution. Such a fibroin-coated pigment was recently invented, and applications for patent on this invention have already been made in Japan (Japanese Patent Application No. 121121/'79, filed Sept. 20, 1979), U.S.A. (U.S. patent application, Ser. No. 187,899, filed Sept. 17, 1980) and EPC countries (Great Britain, West Germany, France and Switzerland) (EPC Patent application No. 801,056,345, filed Sept. 19, 1980).

Specifically, a fibroin-coated pigment suitable for use in the practice of the present invention comprises a carrier pigment in the form of finely divided particles the surfaces of which are substantially coated with a film of regenerated fibroin. In addition, this fibroin-coated pigment is characterized in that at least 50% by weight, preferably at least 80% by weight, and most preferably from 90 to 100% by weight of the regenerated fibroin is constituted of hot-water-insoluble fibroin having the $\beta$-configuration. If the amount of hot-water-insoluble fibroin present in the film of regenerated fibroin is less than 50% by weight, the fibroin becomes extremely hydrophilic. As a result, the fibroin-coated pigment may undergo agglomeration or cohesion under the influence of water or sweat to form secondary particles. Moreover, when applied to the skin, the fibroin-coated pigment is apt to be poor in such properties as spreadability on the skin, feeling and the like.

The term "hot-water-insoluble fibroin" as used herein means that type of fibroin which cannot be dissolved by boiling in hot water at 100° C. for 15 minutes. This hot-water-insoluble fibroin is characterized in that the hydrogen bonding between fibroin molecules consists essentially of the $\beta$-configuration.

The aforesaid film of regenerated fibroin generally has a degree of crystallinity of not less than 10% and preferably from 20 to 43%, though it may vary somewhat according to the conditions of the production process.

The degree of crystallinity of the film of regenerated fibroin present in the fibroin-coated pigment is generally lower than the degree of crystallinity (ranging from about 50 to 55%) of natural silk thread and degummed silk materials.

The aforesaid film of regenerated fibroin is present in an amount of from 2 to 100% by weight and preferably from 5 to 50% by weight based on the weight of the carrier pigment. If the amount is less than 2% by weight, the desired structure in which the surfaces of finely divided particles of the carrier pigment are substantially coated with a film of regenerated fibroin cannot be created. Accordingly, it is difficult to endow the fibroin-coated pigment with properties such as adhesion to the skin, spreadability on the skin, dispersibility, covering power, skin-protecting ability, feeling and the like. On the other hand, if the amount is greater than 100% by weight, the fibroin-coated pigment may tend to show a decrease in covering power.

The aforesaid film of regenerated fibroin generally has a thickness of from 0.01 to 50$\mu$.

The regenerated fibroin present in the fibroin-coated pigment has an average molecular weight of not less than 50,000 and preferably from 80,000 to 150,000.

The fibroin-coated pigment suitable for use in the practice of the present invention has a maximum particle diameter of from 0.05 to 100$\mu$, preferably from 0.05 to 60$\mu$, and most preferably from 0.1 to 30$\mu$.

The carrier pigment used in the fibroin-coated pigment can be any of the well-known pigments for use in cosmetic compositions, including white pigments, color pigments, extender pigments, pearlescent pigments and the like. Typical examples thereof are talc, kaolin, mica, calcium carbonate, titanium oxide, zinc oxide, micaceous titanium, magnesium carbonate, yellow oxide of iron, red oxide of iron, black oxide of iron, ultramarine, zinc stearate, magnesium stearate, magnesium silicate and organic pigments. These pigments may be used alone or in combination.

The aforesaid carrier pigment generally has a maximum particle diameter of from 0.03 to 100$\mu$.

The above-described fibroin-coated pigment has a structure in which the surfaces of finely divided particles of the carrier pigment are substantially coated with a film of regenerated fibroin having moderate water retention properties (i.e., generally having a water retention of about 15% which is substantially the same as that of the skin) and moderate oil absorption properties (i.e., generally having an oil absorption of from 50 to 60% by weight). Accordingly, the fibroin-coated pigment per se is markedly excellent in such properties as adhesion to the skin, affinity for the skin, spreadability on the skin, feeling, moisture retention, buffer capacity, covering power, hydrophilic-lipophilic balance, ultraviolet-absorbing power, skin-protecting ability, fragrance retention and the like. Thus, the above-described fibroin-coated pigment can overcome the disadvantages inherent in the use of conventional pigments, for example, the problems of dehydration, degreasing or drying of the skin, of alkalification of the skin surface, and the like, and can thereby keep the skin intact.

The amount of fibroin-coated pigment used in the makeup composition of the present invention is in the range of from 10 to 90% by weight and preferably from 20 to 80% by weight based on the total weight of the composition, though it may vary somewhat according to the type of the makeup composition. If the amount is less than 10% by weight, the makeup composition is apt to be poor in such properties as moisture retention, fragrance retention, adhesion to the skin, moist and silkily smooth feeling, transfer to and spreadability with an wet applicator (especially of the makeup composition in cake form), and the like. Moreover, the fibroin-coated pigment tends to hardly give a natural silk-like gloss to the skin. On the other hand, if the amount is greater than 90% by weight, the makeup composition can hardly be formed into cakes.

The above-described fibroin-coated pigment can be prepared, for example, by dissolving a degummed silk material in at least one solvent selected from the group consisting of an aqueous cupric-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; dialyzing the resulting fibroin solution, then dispersing a carrier pigment in the resulting aqueous fibroin solution having a fibroin concentration of from 3 to 20% by weight. The pigment-loaded aqueous fibroin solution is then subjected to at least one treatment for coagulating and precipitating the fibroin, the treatment being selected from the group consisting of the addition of a coagulating salt, aeration, coagulation at the isoelectric point, exposure to ultrasonic waves, and agitation at high shear rate. The resulting coagulum, is dehydrated and dried, and then pulverized to form the dried product.

In the fibroin-coated pigmemt used in the practice of the present invention, the film of regenerated fibroin present on the surfaces of the carrier pigment has a microporous structure including ultrafine pores because it is formed by coagulation of an aqueous fibroin solution. Accordingly, the fibroin-coated pigment has high permeability to air and water vapor, thus permitting respiration and physiology of the skin to be maintained. Moreover, the film of regenerated fibroin has a water-absorbing power and a water content (of about 15% by weight) which are substantially the same as those of the protein constituting the skin. Thus, the fibroin-coated pigment has the ability to control the moisture content of the skin surface by absorbing any excess of water and supplying any shortage of water, and the ability to absorb or evaporate sweat and extraneous water. Furthermore, the film of regenerated fibroin has the natural gloss characteristic of silk, as well as a high degree of oil absorption and retention properties. Thus, the fibroin-coated pigment can retain perfume stably for a long time, thereby imparting excellent fragrance retention properties to the products, and can give a natural silk-like gloss or luster to the skin. Such improvements in fragrance retention and gloss constitute one of the outstanding features of the present invention.

The oily material-coated pigment used in the practice of the present invention is a processed pigment the surfaces of which are coated with an oily material. Specifically, an oily material-coated pigment suitable for use in the practice of the present invention is characterized in that the oily material is present in an amount of from 0.1 to 20% by weight and preferably from 10 to 15% by weight based on the weight of the carrier pigment.

The amount of oily material-coated pigment used in the makeup composition of the present invention is generally in the range of from 10 to 90% by weight (and preferably from 20 to 80% by weight) based on the total weight of the composition, though it may somewhat vary according to the amount of oily material present therein and the type of the makeup composition. However, it may be particularly desirable to use the oily material-coated pigment so that the amount of oily material present therein is in the range of from 5 to 20% by weight based on the total weight of the makeup composition.

The oily material used in the oily material-coated pigment is selected from the group consisting of animal fats and oils, vegetable fats and oils, waxes, higher aliphatic hydrocarbons, higher fatty acids, higher alcohols, ester oils, silicone oils, polybutene, metallic soaps and combinations thereof. Specific examples of the animal fats and oils are cod liver oil, beef tallow, butter fat and the like; specific examples of the vegetable fats and oils are olive oil, almond oil, avocado oil, castor oil, cacao butter, palm oil and the like; specific examples of the waxes are bees wax, carnauba wax and the like; specific examples of the higher aliphatic hydrocarbons are liquid paraffin, squalane, vaseline, ceresine and the like; specific examples of the higher fatty acids are lauric acid, myristic acid, palmitic acid, stearic acid, oleic acid, behenic acid, lanolin fatty acid and the like; specific examples of the higher alcohols are lauryl alcohol, stearyl alcohol, cetyl alcohol, oleyl alcohol and the like; specific examples of the ester oils are straight-chain or branched-chain esters such as butyl stearate, hexyl laurate, octyldodecyl myristate, diisopropyl adipate, diisopropyl sebacate and the like; specific examples of the silicone oils are dimethyl polysiloxane and the like; and specific examples of the metallic soaps are magnesium stearate, magnesium isostearate, aluminum isostearate, zinc stearate and the like.

The carrier pigment used in the oily material-coated pigment can be any of the pigments which were enumerated above for the carrier pigment used in the fibroin-coated pigment.

The above-described oily material-coated pigment can be prepared according to any conventional procedure. For example, a pigment as defined above is soaked in an oily material as defined above and the resulting mixture is heat-treated. Alternatively, a pigment is dispersed in an organic solvent solution of an oily material and the resulting dispersion is stirred to allow the oily material to be adsorbed on the surface of the pigment. Then, the product obtained by removing any excess solution is dried. Furthermore, the oily material-coated pigment can also be prepared by dispersing a pigment homogeneously in an organic solvent solution of an oily material and then spary-drying the resulting dispersion.

Owing to the adhesive action (i.e., the action as a binder) of the oily material adsorbed on the surfaces of the carrier pigment, the oily material-coated pigment can combine stably with the coexisting fibroin-coated pigment and bring about an improvement in formability when the makeup composition is pressed into a cake. In addition, it can impart good water resistance to the products and can also provide smooth spreadability on the skin and stable adhesion to the skin.

Although the makeup composition of the present invention has good water resistance, it stability to sweat or extraneous water and other cosmetic effects can be improved by adding an oily material to the makeup composition in an amount of at most 30% by weight (and preferably not greater than 20% by weight).

Where such an additional oily material is used, a pigment (which may be the same but untreated pigments as the carrier pigment of the fibroin-coated pigment or the oily material-coated pigment) can be added to the makeup composition in an amount of at most 20% by weight (and preferably not greater than 15% by weight) without impairing the above-described effects of the present invention to an appreciable degree. However, if the amount is greater than 20% by weight, the makeup composition is apt to be poor in moisture retention and two-way function.

If desired, the aforesaid pigment alone can also be added to the makeup composition in an amount of at most 15% by weight (and preferably not greater than 10% by weight) without impairing the above-described effects of the present invention to an appreciable degree. However, if the amount is greater than 15% by weight, the makeup composition is apt to be poor in moisture retention, two-way function and stability.

The makeup compositions produced in accordance with the present invention include makeup compositions in powder and cake forms, and they can be adapted for use as foundations, eye shadows, mascaras, cheek rouge, lip rouge, eyeliners and the like.

These makeup compositions in powder and cake forms can be produced according to any of the well-known procedure for producing conventional makeup composition.

In accordance with the present invention, as stated before, makeup compositions which consists essentially of a fibroin-coated pigment and an oily material-coated pigment and are in the form of powder or cakes can be readily produced on an industrial scale. The makeup compositions thus obtained can be smoothly and easily used during all seasons, cause no irritation to the skin, have excellent properties such as moisture retention, adhesion to the skin, durability of the makeup, fragrance retention, stability and the like, and can give an agreeable feeling (i.e., a moist and silky smooth feeling) and a natural and soft silk-like gloss or luster to the skin.

Specifically, owing to the desirable properties of the good gloss characteristic of silk, high dispersibility, moderate water absorption, moderate water retention characterized by a latent water content of about 15% by weight, moderate oil absorption characterized by an oil absorption of about 50-60% by weight based on the weight of the fibroin-coated pigment, and good fragrance retention of the regenerated fibroin present in the fibroin-coated pigment, the invention makeup compositions can exhibit excellent properties such as moisture retention, two-way function, hydrophilic nature, lipophilic nature, fragrance retention, the ability to control the moisture content of the skin surface, adhesion to the skin, durability of the makeup, stability and agreeable feeling (i.e., a moist and silkily smooth feeling) and a natural silk-like gloss or luster, thus producing stable cosmetic effects. Especially when the makeup compositions in cake form are applied to the skin by using a wet applicator, the above-described dispersibility, hydrophilic nature and lipophilic nature allow the fibroin-coated pigment to be easily and uniformly dispersed without causing agglomeration or caking of the pigment, so that cosmetic effects characterized by uniform spreadability on the skin and good adhesion to the skin can be produced at any time. Moreover, in spite of the fact that no surface-active agent or wetting agents are used, the oily material-coated pigment and the optionally added oily material and/or pigment can be easily and uniformly dispersed with the aid of the water contained in the wet applicator. Thus, the makeup compositions are free from the problems of skin disorders caused by surface-active agents and pigment agglomeration caused by wetting agents. Even if a wet applicator and a dry applicator are used alternately, the makeup compositions remain so stable that no caking is observed and any desired amount of makeup composition can always be transferred to the applicator and applied to the skin. Furthermore, by using a dry applicator, the makeup compositions can also be transferred to the applicator and evenly spread on the skin to produce stable cosmetic effects. Accordingly, the user can enjoy comfortable, attractive makeup at will and during all seasons, and can appreciate the remarkable and unique effects of the present invention. In addition, owing to the exactly sufficient amount of oily material present on the surfaces of the carrier pigment, the oily material-coated pigment has high affinity for the fibroin-coated pigment regardless of the presence or absence of water, serves to bind the pigment particles, can be dispersed with the aid of water to enable the makeup compositions to exhibit easy transfer to the applicator and good spreadability on the skin, and can provide stable resistance to sweat or water and hence good durability of the makeup.

The present invention is further illustrated by the following examples.

In these examples, the makeup compositions in powder and cake forms were tested according to the following procedures:

(1) Application of Makeup Compositions in Powder Form

The makeup composition to be tested is transferred to a dry sponge puff (in the case of foundations) or a dry sponge mounted on one tip of an applicator (in the case of eye shadows) and then applied to the skin surface.

(2) Application of Makeup Compositions in Cake Form (1) Where a dry applicator is used, the makeup composition to be tested is applied to the skin surface in the same manner as described above for makeup compositions in powder form.

(2) Where a wet applicator is used, a sponge puff or a sponge mounted on one tip of an applicator is impregnated with an appropriate amount of water. Thereafter, the makeup composition to be tested is transferred thereto and then applied to the skin surface.

(3) In order to test the two-way function of a makeup composition in cake form, the makeup composition is applied to the skin surface over a period of 2 months by using a dry applicator (as described in procedure 1) and a wet applicator (as described in procedure 2) on alternate days.

(3) Evaluation of Performance of Makeup Compositions in Powder or Cake Form

The makeup composition to be tested is subjected to performance tests which are carried out by a panel of 10 skilled examiners, and each property thereof is rated on the following basis: Very good=5; Good=4; Moderate=3; Rather poor=2; Poor=1. Then, the property is evaluated by calculating the average score according to the following formula:

Average score = Sum of scores/Number of examiners (In practice, the quotient is rounded to the first decimal place.) The properties which were evaluated in the following examples are spreadability on the skin, adhesion to the skin, moisture retention (moist feeling), durability (or stability) of the makeup, feeling, stability of the product on application with a wet applicator, and the like.

(4) Test for Fragrance Retention

The makeup composition to be tested is stored in a thermostatic chamber at 45° C. for 6 months. Thereafter, the amount of fragrance emitted by the makeup composition is evaluated in comparison with that observed immediately after preparation. The fragrance retention of the makeup composition is rated as "good" if the fragrance emitted thereby remains substantially unchanged; "poor" if the fragrance emitted thereby is considerably decreased; or "very poor" is the fragrance emitted thereby is markedly decreased.

EXAMPLE 1

(1) Preparation of Fibroin-Coated Pigments

One hundred parts by weight of a 50% aqueous solution of calcium chloride was prepared by dissolving 82 parts by weight of calcium chloride in 18 parts by weight of water, and then heating at 110° C. Thereafter, 10 parts by weight of degummed spun silk waste was added, with stirring, to the calcium chloride solution over a period of 5 minutes and dissolved therein completely by stirring for an additional 30 minutes. The resulting fibroin-calcium chloride solution was cooled and then desalted by dialysis through a cellophane tube. After completion of the dialysis, the resulting aqueous fibroin solution had a fibroin concentration of 5.1%.

While 50 parts of weight of this aqueous fibroin solution was being stirred, 10 parts by weight of a carrier pigment (i.e., titanium oxide, kaolin, red oxide of iron, yellow oxide of iron, or black oxide of iron) having particle diameters of 0.1 to 10µ was added thereto and dispersed therein to form a homogeneous suspension. In order to coagulate and precipitate the fibroin (i.e., in order to effect gelation of the fibroin), this suspension was intensively agitated at room temperature by means of an agitator at a shear rate of 100/sec. Initially, the coagulation system was in the form of an aqueous fibroin solution having the carrier pigment suspended therein. In the course of 2-3 hours' agitation, the fibroin gradually coagulated and precipitated on the surfaces of the carrier pigment particles. Ultimately, the whole system formed a mass of gel. This mass of gel was dehydrated by means of a centrifuge and then dired at 105° C. Thereafter, the resulting product was pulverized in a jet mill until the particle diameters thereof were reduced to 0.1–0.5 µ, and then subjected to a wet heat treatment (for insolubilizing the regenerated fibroin in hot water) comprising exposure to saturated steam at 110° C. for 5 minutes. When each of the fibroin-coated pigments thus obtained was dyed with an acid dye (2% Tartrazine NS) and then examined microscopically, the entire surface of each of the carrier pigment particles was found to be brightly and evenly colored in yellow. This demonstrates that the particles of each carrier pigment were uniformly coated with a film of regenerated fibroin. The amount of regenerated fibroin present on the particles of each carrier pigment was 25% by weight based on the weight of the carrier pigment, and the hot-water-insoluble fibroin content of the regenerated fibroin was 88–92% by weight based on the weight of the regenerated fibroin. Moreover, the film of regenerated fibroin had a degree of crystallinity of 26–27%.

(2) Preparation of Oily Material-Coated Pigments

One thousand parts by weight of an oily material mixture consisting of 80% by weight of liquid paraffin and 20% by weight of polybutene (having a degree of polymerization of 2,000) was heated to 100° C., and 100 parts by weight of talc or sericite was added thereto with stirring. Thereafter, the resulting mixture was stirred at 100° C. for 3 hours. While hot (at 100° C.), this mixture was centrifuged to separate any excess oily material mixture from the oily material-coated pigment. In each of the oily material-coated pigments thus obtained, liquid paraffin and polybutene were present in amounts of 12% by weight and 3% by weight, respectively, based on the weight of the carrier pigment. When each of these oily material-coated pigments was dyed with an oil-soluble dye (Sudan III), the entire surfaces of the carrier pigment particles were found to be evenly colored in red. This demonstrates that the particles of each carrier pigment were uniformly coated with the oily materials.

(3) Preparation of Foundations in Powder and Cake Forms

Using a mixer, 44.5 parts by weight of the above oily material-coated talc, 20 parts by weight of the above oily material-coated sericite, 20 parts by weight of the above fibroin-coated kaolin, 12 parts by weight of the above fibroin-coated titanium oxide, 1.0 part by weight of the above fibroin-coated red oxide of iron, 2.0 parts by weight of the above fibroin-coated yellow oxide of iron, and 0.2 part by weight of the above fibroin-coated black oxide of iron were mixed together, and then 0.2 part by weight of perfume was added thereto. The resulting mixture was pulverized and sieved to obtain a foundation in powder form. Thereafter, part of this powder foundation was placed in a metal pan and pressed to obtain a foundation in cake form.

Then, the above foundations were subjected to performance tests and practical tests (2 months) which were carried out by a panel of 10 skilled examiners. As a result, both foundations were found to be very good in such properties as spreadability on the skin, adhesion to the skin, moisture retention, and durability of the makeup. When applied to the skin, they gave a moist, silkily smooth and hence very agreeable feeling and provided the skin with cosmetic effects characterized by a natural silk-like gloss. They also exhibited good fragrance retention. Moreover, the cake foundation was also tested over a period of 2 months by applying it to the skin alternately with a dry puff and with a wet puff. As a result, the cake foundation was found to be very good in transfer to both puffs, adhesion to the skin, and spreadability on the skin. Moreover, the cake foundation was so stable that no caking or hardening thereof was observed until it was used up.

EXAMPLE 2

Using a mixer, 49.5 parts by weight of oily material-coated sericite (which was the same as used in Example 1), 20 parts by weight of fibroin-coated kaolin (which was the same as used in Example 1), 15 parts by weight of fibroin-coated titanium oxide (which was the same as used in Example 1), 1.0 part by weight of fibroin-coated red oxide of iron (which was the same as used in Example 1), 2.0 parts by weight parts by weight of fibroin-coated yellow oxide or iron (which was the same as used in Example 1), and 0.2 part by weight of fibroin-coated black oxide of iron (which was the same as used in Example 1) were mixed together. The resulting mixture was added to and mixed with a molten mixture consisting of 4 parts by weight of liquid paraffin, 1 part by weight of ceresine, 2 parts by weight of lanolin, 4 parts by weight of squalane, and 1 part by weight of stearic acid, and then 0.3 part by weight of perfume was added thereto. The resulting composition was pulverized and sieved to obtain a foundation in powder form. Thereafter, part of this powder foundation was placed in a metal pan and pressed to obtain a foundation in cake form.

Then, the above foundations were subjected to performance tests and practical tests which were carried out in the same manner as described in Example 1. As a result, both foundations were found to be as good as those of Example 1 in such properties as spreadability on the skin, adhesion to the skin, moisture retention, durability of the makeup, silk-like gloss, and fragrance retention. Moreover, the cake foundation was very stable and had an excellent two-way function. Furthermore, a test for the evaluation of water resistance was carried out in which each examiner applied the cake foundation of this example to the right half of her face and the cake foundation of Example 1 to the left half of her face, and then bathed in the sea for 3 hours. As a result, both cake foundations were found to be fairly durable and hence have excellent water resistance. However, the cake foundation of this example was a little more durable than that of Example 1. With regard to feeling, the cake foundations of this example (average score=4.3) were slightly inferior to those of Example 1 (average score=4.9).

EXAMPLE 3

The procedure of Example 2 was repeated except that 1 part by weight of red oxide of iron, 2 parts by weight of yellow oxide of iron, 0.2 part by weight of black oxide of iron, 2 parts by weight of liquid paraffin, and 2.0 parts by weight of polybutene were added to the formulation of Example 2. The resulting powder and cake foundations were nearly as good as those of Example 2 in such properties as adhesion to the skin, feeling, gloss, fragrance retention, water resistance and stability. Moreover, the two-way function of the cake foundation of this example was nearly as good as that of the cake foundation of Example 2. However, the spreadability on the skin (average score=3.6) and moisture retention (average score=3.8) of the foundations of this example were lower than those (average scores=4.3) of the foundations of Example 2. The feeling (average score=3.6) of the foundations of this example was also lower.

EXAMPLE 4

Using a mixer, 35 parts by weight of oily material-coated micaceous titanium (in which magnesium stearate was present in an amount of 5% by weight based on the weight of the micaceous titanium), 35 parts by weight of fibroin-coated micaceous titanium, 33 parts by weight of fibroin-coated sericite, 5 parts by weight of fibroin-coated ultramarine, 12 parts by weight of fibroin-coated red oxide of iron, and 2 parts by weight of fibroin-coated black oxide of iron were mixed intimately. In each of the above fibroin-coated pigments, regenerated fibroin having a hot-water-insolubles content of 90% by weight and a degree of crystallinity of 30-32% was present in an amount of 15% by weight based on the weight of the carrier pigment. The resulting mixture was mixed with a molten mixture consisting of 6 parts by weight of squalane, 3 parts by weight of lanolin, and 4 parts by weight of myristic acid, and then 0.3 part by weight of perfume was added thereto. The resulting composition was pulverized and sieved to obtain an eye shadow in powder form. Thereafter, part of this powder eye shadow was placed in a metal pan and pressed to obtain an eye shadow in cake form.

Then, the above eye shadows were subjected to performance tests and practical tests which were carried out in the same manner as described in Example 1. As a result, both eye shadows were found to be very good in such properties as spreadability on the skin, adhesion to the skin, moisture retention, and durability of the makeup. When applied to the skin, they gave a moist, silkily smooth and hence very agreeable feeling and provided the skin with cosmetic effects characterized by a natural silk-like gloss. They also exhibited very good fragrance retention. Moreover, the cake eye shadow had an excellent two-way function. Thus, the cake eye shadow was so stable that no caking or hardening thereof was observed until it was used up.

EXAMPLE 5

Using a mixer, 50 parts by weight of oily material-coated micaceous titanium (in which squalane and polybutene having an average degree of polymerization of 1,500 were present in amounts of 12% by weight and 20% by weight, respectively, based on the weight of the micaceous titanium), 5 parts by weight of mica (untreated pigment), 27 parts by weight of fibroin-coated talc, 8 parts by weight of fibroin-coated red oxide of iron, 6 parts by weight of fibroin-coated yellow oxide of iron, and 4 parts by weight of fibroin-coated black oxide of iron were mixed intimately. In each of the above fibroin-coated pigments, regenerated fibroin having a hot-water-insoluble fibroin content of 80% by weight was present in an amount of 15% by weight based on the weight of the carrier pigment. The resulting mixture was mixed with 0.3 part by weight of perfume to obtain an eye shadow in powder form. Thereafter, part of this powder eye shadow was placed in a metal pan and pressed to obtain an eye shadow in cake form.

Then, the above eye shadows were subjected to performance tests and practical tests which were carried out in the same manner as described in Example 1. As a result, both eye shadows were found to be good in such properties as spreadability on the skin, adhesion to the skin, moisture retention, and durability of the makeup. When applied to the skin, they gave a moist, silky and hence agreeable feeling and provided the skin with a natural silk-like gloss. They also exhibited good fragrance retention. Moreover, the two-way function of the cake eye shadow of this example was nearly as excellent as that of the cake eye shadow of Example 5. Thus, the cake eye shadow was so stable that no caking or hardening thereof was observed before it was used up.

EXAMPLE 6

Using a mixer, 22 parts by weight of oily material-coated talc (in which magnesium myristate was present in an amount of 5% by weight based on the weight of the talc), 30 parts by weight of fibroin-coated sericite, 20 parts by weight of fibroin-coated titanium oxide, and 18 parts by weight of fibroin-coated carbon black were mixed intimately. In each of the above fibroin-coated pigments, regenerated fibroin having a hot-water-insoluble fibroin content of 50% by weight and a degree of crystallinity of 11-13% was present in an amount of 30% by weight based on the weight of the carrier pigment. The resulting mixture was mixed with 3 parts by weight of lanolin, 4 parts by weight of polybutene (having a degree of polymerization of 2,500), and 3 parts by weight of squalane, and then 0.3 part by weight of perfume was added thereto. The resulting composition was pulverized and sieved to obtain an eyeliner in powder form. Thereafter, part of this powder eyeliner was placed in a metal pan and pressed to obtain an eyeliner in cake form.

Then, the above eyeliners were subjected to performance tests and practical tests which were carried out in the same manner as described in Example 1. As a result, both eyeliners were found to be very good in such properties as spreadability on the skin, adhesion to the skin, moisture retention, durability of the makeup, and fragrance retention. When applied to the skin, they gave a moist, silky smooth and hence agreeable feeling and provided the skin with cosmetic effects characterized by a natural silk-like gloss. Moreover, the cake eyeliner had an excellent two-way function. Thus, the cake eyeliner was so stable that no caking or hardening thereof was observed until it was used up.

COMPARATIVE EXAMPLE 1

An intimate mixture consisting of 62 parts by weight of talc, 5 parts by weight of kaolin, 5 parts by weight of sericite, 6 parts by weight of titanium oxide, 2 parts by weight of red oxide of iron, 2 parts by weight of yellow oxide of iron, 0.04 part by weight of carbon black, and 1 part by weight of perfume was prepared. Then, a molten mixture consisting of 9 parts by weight of squalane, 4 parts by weight of liquid paraffin, and 3 parts by weight of stearic acid was sprayed on the above mixture of pigments. In addition, 3 parts by weight of polyethylene glycol was sprinkled thereon. The resulting composition was placed in a metal pan and pressed to obtain a foundation in cake form.

Then, the above cake foundation was tested by applying it to the skin with a dry sponge. After 3 days, it hardened as a result of caking of the pigments and thereafter failed to transfer to the dry sponge. On the other hand, this cake foundation was tested with a wet sponge. Thus, it was found to be poor in spreadability on the skin and adhesion to the skin. After 20 days, it hardened as a result of caking of the pigments. Moreover, its fragrance retention was also found to be poor because it emitted only faint fragrance after 6 months' storage at 45° C.

COMPARATIVE EXAMPLE 2

An intimate mixture consisting of 10 parts by weight of polyethylene powder, 28 parts by weight of talc, 5 parts by weight of kaolin, 25 parts by weight of sericite, 8 parts by weight of titanium oxide, 1.0 part by weight of red oxide or iron, 1.0 part by weight of yellow oxide of iron, and 0.05 part by weight of carbon black was prepared. Then, an intimate mixture consisting of 15 parts by weight of silicone oil, 1 part by weight of squalane, 1 part by weight of liquid paraffin, 2 parts by weight of stearic acid, and 1 part by weight of perfume was added to the above mixture of pigments and thoroughly mixed therewith. The resulting composition was placed in a metal pan and pressed to obtain a foundation in cake form.

The, the above cake foundation was tested over a period of 2 months by using a wet sponge and a dry sponge alternately. As a result, it was found that, in either case, this cake foundation was poor in spreadability on the skin and adhesion to the skin and imparted an oily gloss to the skin. Especially when a dry sponge was used, this cake foundation gave an oily, strongly greasy and hence disagreeable feeling. Moreover, its fragrance retention was also found to be poor because it emitted only faint fragrance after 6 months' of storage at 45° C. Thus, this cake foundation was inferior to the cake foundations of the foregoing examples in all of the properties evaluated (i.e., spreadability on the skin, adhesion to the skin, feeling, gloss and fragrance retention). This demonstrates that the present invention can produce remarkable and unique cosmetic effects.

COMPARATIVE EXAMPLE 3

For purposes of comparison, a foundation in cake form was prepared by repeating the procedure of Example 1 except that the fibroin-coated pigments were replaced by the same (but untreated) pigments as constituted the carrier pigments thereof (for example, the fibroin-coated kaolin was replaced by kaolin). The resulting cake foundation and the cake foundation of Example 1 were subjected to practical tests in which a panel of 30 women evaluated these cake foundations comparatively by using either a wet sponge puff or a dry sponge puff. The test results thus obtained are shown in the following table. Each of the values listed in this table represents the number of the women who gave an affirmative answer about the corresponding property.

| Property | Dry sponge puff | | Wet sponge puff | |
|---|---|---|---|---|
| | Ex. 1 | Comp. Ex. 3 | Ex. 1 | Comp. Ex. 3 |
| Easy transfer to the puff | 30 | 18 | 20 | 10 |
| Moist feeling | 30 | 10 | 30 | 10 |
| Good adhesion to the skin | 30 | 1 | 30 | 2 |
| High affinity for the skin | 30 | 2 | 30 | 3 |
| Spreadability on the skin | 30 | 2 | 30 | 3 |
| Good fragrance retention | 30 | 9 | 25 | 10 |

In addition, the two-way function of these cake foundations was tested over a period of 30 days by using a dry sponge puff and a wet sponge puff on alternate days. The test results thus obtained are shown in the following table.

| Result | Ex. 1 | Comp. Ex. 3 |
|---|---|---|
| The cake hardened within 5 days and thereafter failed to transfer to the puffs | 0 | 15 |
| The cake hardened within 10 days and thereafter failed to transfer to the puffs. | 0 | 10 |
| The cake hardened within 15 days and thereafter failed to transfer to the puffs. | 0 | 3 |
| The cake hardened within 20 days and thereafter failed to transfer to the puffs. | 0 | 1 |
| The cake hardened within 30 days and thereafter failed to transfer to the puffs. | 0 | 0 |
| The cake transferred easily to both the dry sponge puff and the wet sponge puff. | 30 | 0 |

COMPARATIVE EXAMPLE 4

For purposes of comparison, an eye shadow in cake form was prepared by repeating the procedure of Example 4 except that the oily material-coated pigments were replaced by the same (but untreated) pigments as constituted the carrier pigments thereof and the fibroin-coated pigments were replaced by the same (but untreated) pigments as constituted the carrier pigments thereof. The resulting cake eye shadow and the cake eye shadow of Example 4 were subjected to practical tests in which a panel of 30 women evaluated these cake eye shadows comparatively by using either an applicator with a dry sponge or an applicator with a wet sponge. The test results thus obtained are shown in the following table. Each of the values listed in this table represents the number of the women who gave an affirmative answer about the corresponding property.

| Property | Dry sponge | | Wet sponge | |
|---|---|---|---|---|
| | Ex. 4 | Comp. Ex. 4 | Ex. 4 | Comp. Ex. 4 |
| Easy transfer to the applicator | 30 | 20 | 30 | 1 |
| Spreadability on the eyelids | 30 | 10 | 30 | 2 |
| Glossy finish | 30 | 5 | 30 | 4 |
| Good moisture retention | 30 | 5 | 30 | 5 |
| Freedom from agglomeration | 30 | 5 | 30 | 1 |
| Freedom from darkening of the color | 30 | 5 | 30 | 2 |

In addition, the two-way function of these cake eye shadows was tested over a period of 30 days by using an applicator with a dry sponge and an applicator with a wet sponge on alternate days. The test results thus obtained are shown in the following table.

| Result | Ex. 4 | Comp. Ex. 4 |
|---|---|---|
| The cake hardened within 10 days and thereafter failed to transfer to the sponges. | 0 | 18 |
| The cake hardened within 20 days and thereafter failed to transfer to the sponges. | 0 | 11 |
| The cake hardened within 30 days and thereafter failed to transfer to the sponges. | 0 | 1 |
| The cake transferred easily to both the dry sponge and the wet sponge. | 30 | 0 |

What is claimed is:

1. A cosmetic makeup composition consisting essentially of a homogenous mixture of from 10 to 90% by weight of finely divided, fibroin-coated, pigment particles and finely divided, oily material-coated, pigment particles, said fibroin-coated, pigment particles consisting essentially of first carrier pigment particles each substantially uniformly coated with a film of regenerated fibroin wherein the amount of said regenerated fibroin is from 2 to 100% by weight based on the weight of said first carrier pigment particles, at least 50% by weight of said regenerated fibroin consisting of hot-water-insoluble fibroin having the β-configuration, and said oily material-coated, pigment particles consisting essentially of second carrier pigment particles the surfaces of which are substantially uniformly coated with substantially water-insoluble, oily material suitable for use in cosmetics, the amount of said oily material being from 10 to 15% by weight based on the weight of said second carrier pigment particles, said composition being in the form of a compressed cake.

2. A makeup composition as claimed in claim 1 wherein at least 80% by weight of said regenerated fibroin consists of hot-water-insoluble fibroin having the β-configuration.

3. A makeup composition as claimed in claim 1 wherein said film of regenerated fibroin has a degree of crystallinity of at least 10%.

4. A makeup composition as claimed in claim 1 wherein the amount of said regenerated fibroin is from 5 to 50% by weight based on the weight of said first carrier pigment particles.

5. A makeup composition as claimed in claim 1 which contains from 20 to 80% by weight of said finely divided, fibroin-coated pigment particles based on the total weight of said composition.

6. A makeup composition as claimed in claim 1 wherein said oily material included in said oily material-coated pigment particles is selected from the group consisting of animal fats and oils, vegetable fats and oils, waxes, higher aliphatic hydrocarbons, higher fatty acids, higher alcohols, ester oils, metallic soaps, polybutene, silicone oils and combinations thereof.

7. A makeup composition as claimed in claim 1 wherein said first and second carrier pigment particles included in said fibroin-coated pigment particles and said oily material-coated pigment particles, respectively, are selected from the group consisting of talc, kaolin, mica, calcium carbonate, titanium oxide, zinc oxide, micaceous titanium, magnesium carbonate, yellow oxide of iron, red oxide of iron, black oxide of iron, ultramarine, zinc stearate, magnesium stearate, magnesium silicate, carbon black, organic pigments and combinations thereof.

8. A makeup composition as claimed in claim 1 wherein said oily material-coated pigment particles are present in an amount of from 10 to 90% by weight based on the total weight of said composition.

9. A makeup composition as claimed in claim 1 wherein said oily material-coated pigment particles are present in an amount of from 20 to 80% by weight based on said total weight of the composition.

10. A makeup composition as claimed in claim 1 which further contains up to 30% by weight of an oily material suitable for use in cosmetics, based on the combined weight of said fibroin-coated pigment particles and said oily material-coated pigment particles.

11. A makeup composition as claimed in claim 1 which further contains up to 15% by weight of untreated pigment, based on the combined weight of said fibroin-coated pigment particles and said oily material-coated pigment particles.

12. A makeup composition as claimed in claim 1 wherein said makeup composition is a cosmetic selected from the group consisting of foundation, eye shadow, mascara, cheek rouge, lip rouge and eyeliner.

13. A makeup composition as claimed in claim 1 wherein said film of regenerated fibroin has a degree of crystallinity of 20 to 43%, and said fibroin is not dissolved by immersion in boiling water at 100° C. for 15 minutes.

14. A makeup composition as claimed in claim 1 wherein said film of regenerated fibroin has a thickness of from 0.01 to 50μ, said fibroin-coated, pigment particles have a maximum particle size in the range of 0.05 to 60μ, and said regenerated fibroin has an average molecular weight of not less than 50,000.

15. A makeup composition as claimed in claim 1 wherein said makeup composition consists essentially of 10 to 90% by weight of said fibroin-coated, pigment particles, 10 to 90% by weight of said oily material-coated, pigment particles, 0 to 15% by weight of a pigment, and 0 to 30% by weight of an oily material.

16. A makeup composition as claimed in claim 1 wherein said makeup composition consists essentially of 20 to 80% by weight of said fibroin-coated, pigment particles, 20 to 80% by weight of said oily material-coated, pigment particles, 0 to 10% by weight of untreated pigment, and 0 to 20% by weight of an oily material suitable for use in cosmetics.

17. A makeup composition as claimed in claim 1 wherein said regenerated fibroin has a molecular weight in the range of 80,000 to 150,000.

18. A makeup composition as claimed in claim 1 wherein said regenerated fibroin is capable of absorbing from 50 to 60% by weight of oil and about 15% by weight of water.

19. A makeup composition as claimed in claim 1 in which said fibroin-coated, pigment particles have been regenerated by a process which comprises the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution and an aqueous solution of the chloride or nitrate or thiocyanate of calcium, magnesium or zinc, and an aqueous sodium thiocyanate solution; dialyzing the resulting fibroin solution; dispersing said first carrier pigment particles in the resulting aqueous fibroin solution having a fibroin concentration of from 3 to 20% by weight; subjecting the pigment-loaded aqueous fibroin solution to at least one treatment for coagulating and precipitating the fibroin, the treatment being selected from the group consisting of the addition of a coagulating salt, aeration, exposure to ultrasonic waves, and agitation at high shear rate; drying the resulting coagulum; and then pulverizing the dried product.

* * * * *